US011647933B2

(12) United States Patent
Sudo et al.

(10) Patent No.: US 11,647,933 B2
(45) Date of Patent: May 16, 2023

(54) BIOLOGICAL INFORMATION DETECTION DEVICE

(71) Applicants: ATOM MEDICAL CORPORATION, Tokyo (JP); SEKISUI PLASTICS CO., LTD., Osaka (JP)

(72) Inventors: Kazuhiko Sudo, Saitama (JP); Naoko Odagiri, Saitama (JP); Kazunari Oowada, Saitama (JP); Ichiro Matsubara, Tokyo (JP); Takaaki Hatori, Osaka (JP); Takahiko Fujita, Osaka (JP); Kazuhiro Yoshikawa, Osaka (JP)

(73) Assignees: ATOM MEDICAL CORPORATION, Tokyo (JP); SEKISUI PLASTICS CO., LTD, Osaka (JP)

( * ) Notice: Subject to any disclaimer, the term of this patent is extended or adjusted under 35 U.S.C. 154(b) by 267 days.

(21) Appl. No.: 16/652,516

(22) PCT Filed: Sep. 27, 2018

(86) PCT No.: PCT/JP2018/035857
§ 371 (c)(1),
(2) Date: Mar. 31, 2020

(87) PCT Pub. No.: WO2019/069773
PCT Pub. Date: Apr. 11, 2019

(65) Prior Publication Data
US 2021/0361214 A1    Nov. 25, 2021

(30) Foreign Application Priority Data
Oct. 5, 2017  (JP) .............................. JP2017-194844

(51) Int. Cl.
| | | |
|---|---|---|
| *A61B 5/259* | (2021.01) | |
| *A61B 5/273* | (2021.01) | |
| *A61B 5/00* | (2006.01) | |

(52) U.S. Cl.
CPC .............. *A61B 5/259* (2021.01); *A61B 5/273* (2021.01); *A61B 5/4362* (2013.01);
(Continued)

(58) Field of Classification Search
CPC ....... A61B 5/259; A61B 5/273; A61B 5/4362; A61B 5/7203; A61B 5/6823; A61B 2503/02
See application file for complete search history.

(56) References Cited

U.S. PATENT DOCUMENTS

| | | |
|---|---|---|
| 4,040,412 A | 8/1977 | Sato |
| 4,239,046 A | 12/1980 | Ong |

(Continued)

FOREIGN PATENT DOCUMENTS

| | | |
|---|---|---|
| CN | 105411564 A | 3/2016 |
| DE | 10307446 A1 | 10/2003 |

(Continued)

OTHER PUBLICATIONS

Yasuaki, Koike, Translation of JP-10272110-A, Biomedical Electrode, Oct. 13, 1998 (Year: 1998).*

(Continued)

*Primary Examiner* — Adam Z Minchella
(74) *Attorney, Agent, or Firm* — Crowell & Moring LLP

(57) ABSTRACT

Provided is a biological information detection device capable of restraining noise from being mixed with a signal relating to biological information. A biological information detection device includes an electrode pad that is able to detect a signal (bioelectric signal) relating to biological information of a subject (for example, a fetus in a mother's (Continued)

body), a connector that is connectable to the electrode pad, and a cable that is connected to the connector and is able to transmit the signal. The electrode pad and the connector are provided with fixing members and that are attachable to and detachable from each other, respectively.

4 Claims, 5 Drawing Sheets

(52) U.S. Cl.
CPC .......... *A61B 5/7203* (2013.01); *A61B 5/6823* (2013.01); *A61B 2503/02* (2013.01)

(56) References Cited

U.S. PATENT DOCUMENTS

| | | | | |
|---|---|---|---|---|
| 5,218,973 | A | * | 6/1993 | Weaver ................ A61N 1/0496 607/152 |
| 5,566,672 | A | * | 10/1996 | Faasse, Jr. ........... A61N 1/0492 607/152 |
| 6,032,064 | A | * | 2/2000 | Devlin .................. A61B 5/291 600/397 |
| 2004/0082843 | A1 | * | 4/2004 | Menon .................. A61B 5/259 600/395 |
| 2016/0250466 | A1 | * | 9/2016 | Boggs, II ........... A61N 1/36017 607/46 |
| 2016/0262649 | A1 | * | 9/2016 | Hayes-Gill .......... A61B 5/4362 |
| 2017/0164860 | A1 | * | 6/2017 | Hung .................... A61B 5/282 |

FOREIGN PATENT DOCUMENTS

| | | |
|---|---|---|
| JP | H01-288232 A | 11/1989 |
| JP | H03-000707 U | 1/1991 |
| JP | 10272110 A * | 10/1998 |
| JP | H10-272110 A | 10/1998 |
| JP | 2014-83308 A | 5/2014 |
| JP | 2015-109172 A | 6/2015 |
| JP | 2017023754 A | 2/2017 |

OTHER PUBLICATIONS

Extended European Search Report in Europe Application No. 18864934.7, dated Jun. 1, 2021, 7 pages.
Office Action in Japan Application No. 2020-090308, including English translation, dated Mar. 30, 2021, 6 pages.

* cited by examiner

BIOLOGICAL INFORMATION DETECTION DEVICE

This application is a 371 application of PCT/JP2018/035857 having an international filing of Sep. 27, 2018, which claims priority to JP2017-194844 filed Oct. 5, 2017, the entire content of each of which is incorporated herein by reference.

BACKGROUND OF THE INVENTION

Field of the Invention

The present invention relates to a biological information detection device including an electrode pad that is mounted on a patient and detects a signal relating to biological information of the patient, a fetus, and the like, and a connector that is connected to the electrode pad.

The present application claims priority based on Japanese Patent Application No. 2017-194844, filed Oct. 5, 2017, the content of which is incorporated herein by reference.

Background Art

As a biomedical electrode that is stuck on a skin surface of a living body and acquires biological signal of the living body, for example, a biomedical electrode described in Patent Literature 1 is known.

The biomedical electrode described in Patent Literature 1 includes a pair of an upper holding member and a lower holding member that have one end disposed in a laminated manner and have an adhesive layer formed over the entire lower surface, and a film-shaped electrode member that is sandwiched between the holding members. The upper holding member covers the entire surface of the electrode member such that one side of the upper holding member on a laminated side coincides with one side of the electrode member. The electrode member is held to be closely adhered near one side of the lower holding member on a laminated side.

In acquiring the biological signal with the biomedical electrode, the holding members and the electrode member are stuck on the skin surface of the living body through adhesive layers, and the electrode member is clipped by a clipping member provided at a tip of a cable. With this, a biological signal detected by the electrode member is transmitted through the cable.

CITATION LIST

Patent Literature

[Patent Literature 1] Japanese Unexamined Patent Application, First Publication No. H10-272110

SUMMARY OF INVENTION

Technical Problem

Incidentally, in the biomedical electrode (electrode pad) described in Patent Literature 1, in clipping the electrode member with the clipping member, the upper holding member and the electrode member are integrally clipped by the clipping member, and one clipping portion of the clipping member is sandwiched between the electrode member and the lower holding member.

However, in the configuration of Patent Literature 1, for example, in a case where the living body is a mother's body, the clipping member (connector) may move due to the movement of the mother's body and the movement of the fetus in the mother's body, and noise may be mixed with the biological signal. Specifically, the movement of the connector due to the movement of the mother's body or the movement of the fetus causes shake or twist of the cable connected to the connector or causes the cable to be pulled to bring the electrode pad in a state demounted from the mother's body, and then, noise is mixed with the biological signal detected by the electrode pad.

In order to restrain noise from being mixed with the biological signal, a method that the cable connected to the connector is fixed to the mother's body or the like with a tape is considered; however, it is complicated to fix the cable to the mother's body with the tape each time the biological information is detected, and it is not easy to remove the tape or clean an adhesive layer (dirt) of the tape attached to the cable. In addition, since the cable is fixed to the mother's body by the tape, there is a problem in that rough skin is caused in the mother's body.

The present invention has been accomplished in consideration of such a situation, and an object of the present invention is to provide a biological information detection device capable of restraining noise from being mixed with a signal relating to biological information.

Solution to Problem

A biological information detection device of the present invention includes an electrode pad that is able to detect a signal relating to biological information of a subject, a connector that is connectable to the electrode pad, and a cable that is connected to the connector and is able to transmit the signal. The electrode pad and the connector are provided with fixing members that are attachable to and detachable from each other, respectively.

In the present invention, since the electrode pad and the connector connectable to the electrode pad are provided with the fixing members that are attachable to and detachable from each other, it is possible to fix the connector connected to the electrode pad to the electrode pad. With this, in detecting the signal relating to the biological information of the subject with the electrode pad, even though there is the movement of the subject (for example, in a case where the subject is a fetus in the mother's body, the movement of the mother's body or the movement of the fetus in the mother's body) and the cable is pulled, since the electrode pad and the connector are fixed by the fixing members, it is possible to restrain noise from being mixed with the detected signal relating to the biological information.

As a preferable aspect of the biological information detection device of the present invention, the electrode pad may include an adhesive sheet having an adhesive surface on one surface, a sensor part that is positioned on the adhesive surface and is able to detect the signal, a conductive gel sheet that is disposed to overlap the sensor part and is adherable, a signal line that is connected to the sensor part and extends to an outside of an outer peripheral edge of the conductive gel sheet, and a connection portion that is provided at a tip of the signal line and is connectable to the connector. The adhesive sheet may have an opening portion that is formed to expose the connection portion to a surface opposite to the adhesive surface. The fixing member may be disposed at a position adjacent to the opening portion on the surface of the adhesive sheet opposite to the adhesive surface.

Here, in a configuration in which the connector is connected directly to the sensor part of the electrode pad, since pressure at the time of the connection of the connector, shake of the cable, or the like acts directly on the sensor part, noise is likely to be mixed with the signal relating to the biological information detected by the sensor part.

In contrast, in the above-described aspect, the signal line connected to the sensor part extends to the outside of the outer peripheral edge of the gel sheet, and the connector is connectable to the connection portion at the tip of the signal line. That is, since a position of the sensor part and a connection position to the connector are offset, it is possible to restrain the pressure at the time of the connection of the connector or shake of the cable from acting directly on the sensor part. With this, it is possible to suppress shake or movement of the sensor part, and to restrain noise from being mixed with the signal.

Since the fixing member can be disposed on the surface of the adhesive sheet constituting the electrode pad opposite to the adhesive surface, it is possible to facilitate attachment and detachment of the connector to and from the electrode pad.

As a preferable aspect of the biological information detection device of the present invention, the electrode pad may include a plurality of the sensor parts, a plurality of conductive gel sheets, and a plurality of the signal lines, tip portions of the plurality of the signal lines may be bundled, the one connection portion may be provided at a tip of a portion where the signal lines are bundled, and the connection portion may be positioned between adjacent conductive gel sheets in the adhesive sheet.

In the above-described aspect, since the electrode pad includes a plurality of sensor parts, it is possible to detect more signals relating to biological information of the fetus in the mother's body with a plurality of sensor parts.

Since only the one connection portion is provided, and the connection portion is positioned between adjacent gel sheets, it is possible to reduce the size of the electrode pad compared to a case where the connection portion is provided for each signal line. Since the number of connection portions is one, it is possible to reduce the number of connectors and the number of cables, and to restrain noise from being mixed with the detected signal relating to the biological information.

As a preferable aspect of the biological information detection device of the present invention, a connection direction of the connector may be a surface direction of the adhesive sheet and may be a direction different from an extension direction of the signal line from the sensor part to the outer peripheral edge of the conductive gel sheet. In plan view of the adhesive sheet, a maximum dimension of an area in the adhesive sheet, in which the connector is provided, along the connection direction of the connector may be equal to or smaller than a maximum dimension of an area, in which the conductive gel sheet is provided, along the connection direction of the connector.

Here, in a case where the connection direction of the connector is the same direction as the extension direction of the signal line from the sensor part to the outer peripheral edge of the conductive gel sheet, since the fixing member is disposed to extend in the extension direction of the signal line, the shape of the adhesive sheet is elongated in the extension direction of the signal line, and the dimension of the adhesive sheet (electrode pad) in the extension direction of the signal line increases. In a case where the connection portion is extended in the same direction as the extension direction of the signal line, when the connector is connected to the connection portion, force generated at the time of the connection acts along the extension direction of the signal line. Thus, force is applied directly to the sensor part through the signal line, and there is an increasing possibility that the electrode pad is demounted from the subject (or in a case where the subject is the fetus in the mother's body, the mother's body), and that the electrode pad is damaged.

In contrast, in the above-described aspect, the connection direction of the connector is the direction different from the extension direction of the signal line from the sensor part to the outer peripheral edge of the conductive gel sheet. Thus, in a case where the fixing member is disposed at the position adjacent to the opening portion, the shape of the adhesive sheet is not elongated in the extension direction of the signal line, and the maximum dimension of in the adhesive sheet along the connection direction of the connector can be equal to or smaller than the maximum dimension of the area, in which the conductive gel sheet is provided, in the above-described direction. That is, it is possible to reduce the size of the electrode pad.

Even though the connector is connected to the connection portion, since force generated due to the connection of the connector is not applied directly to the signal line and the sensor part, it is possible to reduce a possibility that the electrode pad is demounted from the subject or the like, and the electrode pad is damaged.

As a preferable aspect of the biological information detection device of the present invention, the electrode pad may have an electromagnetic shield layer that covers the sensor part between the adhesive surface and the sensor part.

In the above-described aspect, as the electromagnetic shield layer is provided between the adhesive surface and the sensor part, since the sensor part is hardly affected by electromagnetic waves, it is possible to further restrain noise from being mixed with the signal relating to the biological information detected by the sensor part.

As a preferable aspect of the biological information detection device of the present invention, the fixing member may be constituted of a hook-and-loop fastener.

In the above-described aspect, since the fixing member is constituted of the hook-and-loop fastener, it is possible to facilitate attachment and detachment of the electrode pad and the connector.

Advantageous Effects of Invention

According to the present invention, it is possible to restrain noise from being mixed with the signal relating to the biological information.

DESCRIPTION OF EMBODIMENTS

Figure 1:
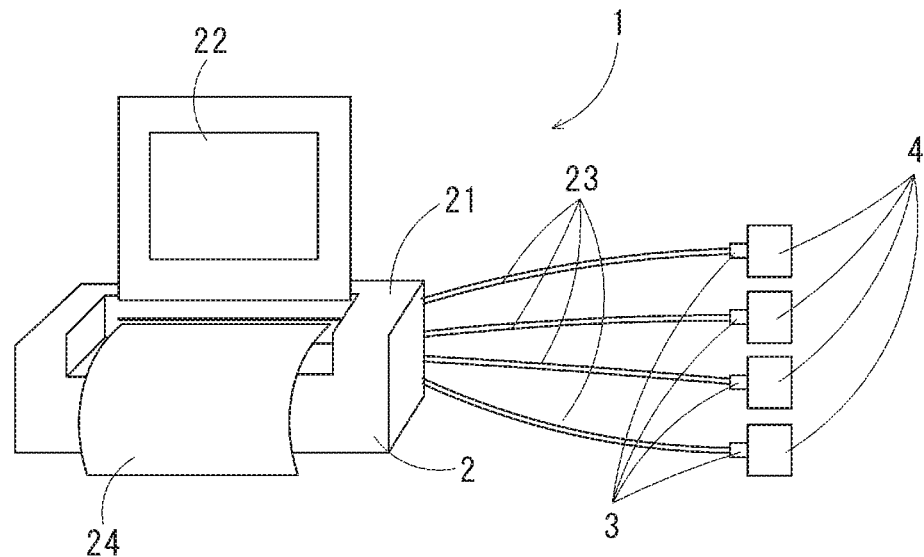
FIG. 1 is a schematic view showing the schematic configuration of a biological information detection device according to an embodiment of the present invention.

Hereinafter, an embodiment of a biological information detection device of the present invention will be described referring to the drawings.

[Schematic Configuration of Biological Information Detection Device]

As shown in FIG. 1, a biological information detection device 1 of the embodiment includes a main body 2 and a plurality of electrode pads 4. The main body 2 includes a housing 21, a display unit 22, and a plurality of cables 23, and recording paper 24 is provided in the housing 21. Each of a plurality of cables 23 is connected to each connector 3, and each connector 3 is provided to be connectable to each corresponding electrode pad 4.

The electrode pad 4 receives an electric signal relating to biological information of a fetus (subject) in a mother's body 6 (see FIG. 9) and transmits the electric signal (hereinafter, referred to as a bioelectric signal) relating to the biological information to the main body 2 through the connector 3 and the cable 23. In the bioelectric signal, for example, a heart rate signal, a respiratory signal, a myoelectric signal, and the like are included.

The main body 2 receives the bioelectric signal output from the electrode pad 4, calculates a heart rate (fetus heart rate) of the fetus in the mother's body 6, displays the bioelectric signal and the fetus heart rate on the display unit 22, and prints the fetus heart rate on the recording paper 24 provided in the housing 21. The main body 2 may store the fetus heart rate in a memory (not shown) in addition to or instead of displaying or printing the fetus heart rate.

The biological information detection device 1 of the embodiment has a feature in a fixing structure of the connector 3 to the electrode pad 4 when the connector 3 is fitted with the electrode pad 4.

In FIG. 1, although four cables 23 are connected to the housing 21 has been shown, actually, many (for example, five in an example of FIG. 9) cables 23 are provided.

In the following description, a surface that comes into contact with the mother's body 6 when the electrode pad 4 is mounted on the mother's body 6 is referred to as a contact surface 4a, and a surface that is positioned on a side opposite to the mother's body 6 is referred to as a top surface 4b.

[Configuration of First Electrode Pad]

Figure 5:
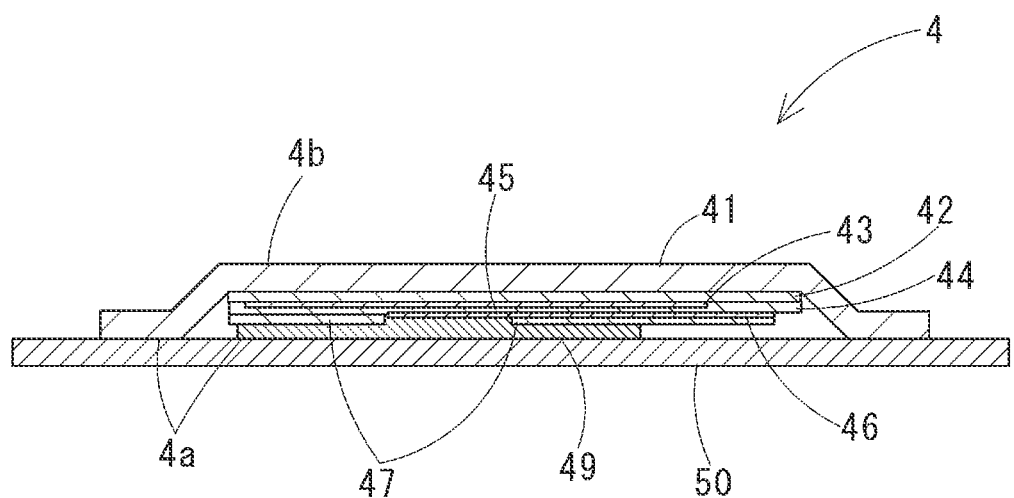
FIG. 5 is a sectional view showing a section of the first electrode pad taken along a line A1 to A1 shown in FIG. 4.

A first electrode pad 4 is mountable on the mother's body 6 and detects the signal (bioelectric signal) relating to the biological information of the fetus in the mother's body 6. As shown in FIG. 5, the first electrode pad 4 includes, in order from the top surface 4b side, an adhesive sheet 41 that has an adhesive surface on a surface opposite to the top surface 4b, a PET film 42 that is adhered to the adhesive surface, an electromagnetic shield layer 43 that is formed on a surface of the PET film 42 opposite to the top surface 4b, a first insulating layer 44 that is positioned on the contact surface 4a side of the electromagnetic shield layer 43, a sensor part 45 and a signal line 46 (connection portion 461) that are positioned on the contact surface 4a side of the first insulating layer 44, a second insulating layer 47 that is positioned on the contact surface 4a side of the first insulating layer 44 and is positioned around the sensor part 45, a conductive gel sheet 49 that is positioned on the contact surface 4a side of the sensor part 45 and the second insulating layer 47 and has a circular shape in plan view, and a release film 50 that is positioned on the contact surface 4a side of the conductive gel sheet 49. The adhesive sheet 41 and the release film 50 are provided such that outer peripheral edges protrude from the conductive gel sheet 49 and the like, and outer sides are adhered to each other.

Among these, the sensor part 45 and the signal line 46 are constituted of a coating layer through vapor deposition or the like of silver or silver chloride. The electromagnetic shield layer 43 is constituted of a coating layer through vapor deposition or the like of silver or carbon. The connection portion 461 (see FIG. 2) described below is constituted by coating a carbon layer 462 (see FIG. 6) with silver or silver chloride.

Figure 2:
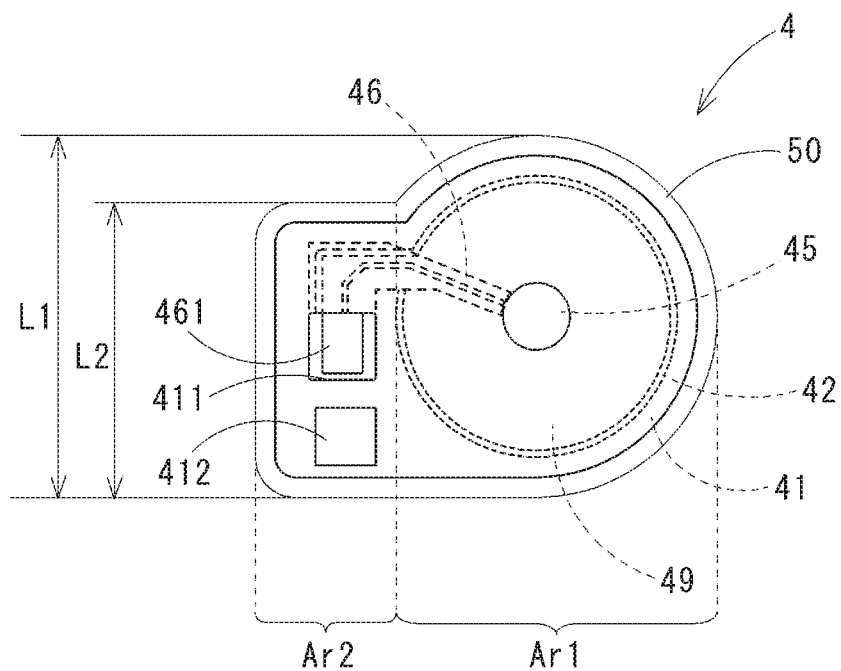
FIG. 2 is a plan view of a first electrode pad of the biological information detection device in the embodiment when viewed from an adhesive sheet side.
Figure 3:
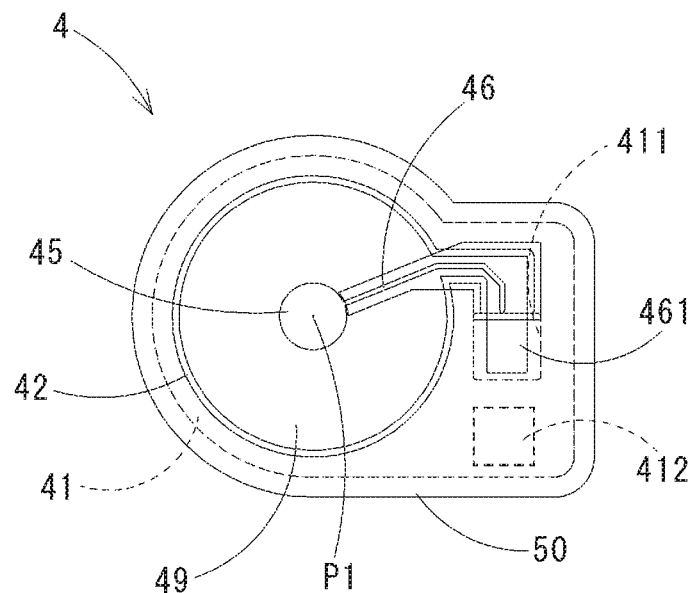
FIG. 3 is a plan view of the first electrode pad in the embodiment when viewed from a release film side.

As shown in FIGS. 2 and 3, the first electrode pad 4 is provided such that the sensor part 45 is provided substantially at the center of the conductive gel sheet 49, the signal line 46 connected to the sensor part 45 extends in a radial direction of the conductive gel sheet 49, and the connection portion 461 is disposed outside the outer peripheral edge of the conductive gel sheet 49. The connection portion 461 is a portion that is connectable to the connector 3, and the connector 3 is connected to the connection portion 461 along an up-down direction in FIG. 2.

Hereinafter, the respective configurations of the first electrode pad 4 will be described in detail.

The adhesive sheet 41 is constituted of, for example, a non-woven fabric having an adhesive surface on one surface (contact surface side). As shown in FIG. 2, the adhesive sheet 41 includes a first area Ar1 where the conductive gel sheet 49 is disposed, and a second area Ar2 where the connection portion 461 is disposed. In the description of FIG. 2, respective directions will be described according to up, down, right, and left directions on the paper.

The first area Ar1 has a shape along the outer peripheral edge of the conductive gel sheet 49. The first area Ar1 is formed to be greater than the outer peripheral edge of the conductive gel sheet 49 and is formed to substantially have a circular shape in plan view.

The second area Ar2 is formed to substantially have a rectangular shape in plan view, and is provided to protrude to one side (a left side of FIG. 2) of the first area Ar1.

In this case, in plan view of the adhesive sheet 41, a maximum dimension L2 of the area (second area Ar2) in the adhesive sheet 41, in which the connector 3 is provided, in an up-down direction (a direction along a connection direction of the connector 3) is smaller than a maximum dimension L1 of the area (first area Ar1), in which the conductive gel sheet 49 is provided, in the up-down direction (the direction along the connection direction of the connector 3).

In the second area Ar2 of the adhesive sheet 41, an opening portion 411 that exposes the connection portion 461 on the surface (top surface) opposite to the adhesive surface. A fixing member 412 that is attachable to and detachable from a fixing member 33 (see FIGS. 4 and 6) of the connector 3 is provided on the surface opposite to the adhesive surface near the opening portion 411. The fixing member 412 is provided in a tip direction of the connection portion 461 with respect to the opening portion 411. That is, the opening portion 411 and the fixing member 412 are arranged in the connection direction of the connector 3.

The fixing member 412 is constituted of, for example, a hook-and-loop fastener, and is disposed at a position adjacent to the opening portion 411 (near a lower side of the opening portion 411).

In general, the hook-and-loop fastener is configured such that a hook-raised side and a densely loop-raised side are pressed and attached, and attachment and detachment can be freely made. In the embodiment, the fixing member 412 is constituted of a densely loop-raised hook-and-loop fastener, and the fixing member 33 of the connector 3 described below is constituted of a hook-raised hook-and-loop fastener.

The PET film 42 is provided on the adhesive surface of the adhesive sheet 41, and is directly adhered and fixed to the adhesive sheet 41. As shown in FIGS. 2 to 5, the PET film 42 is formed to be smaller than the adhesive sheet 41 in plan view and to have a shape capable of supporting the conductive gel sheet 49, the signal line 46, and the connection portion 461 in a lump.

The electromagnetic shield layer 43 suppresses incidence of electromagnetic waves on the sensor part 45. The electromagnetic shield layer 43 is formed by depositing silver or carbon on a surface of the PET film 42 on the contact surface side. As shown in FIG. 5, the electromagnetic shield layer 43 is positioned between the first insulating layer 44 and the PET film 42, that is, between the adhesive surface of the adhesive sheet 41 and the sensor part 45, and is formed to have a shape of covering the conductive gel sheet 49, the sensor part 45, and the signal line 46 in plan view.

Figure 4:
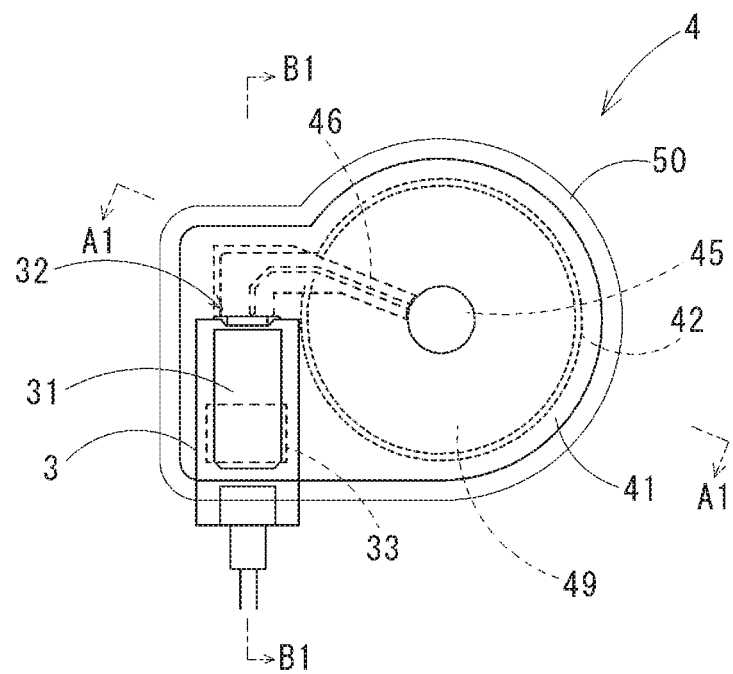
FIG. 4 is a plan view showing a state in which a connector is connected to the first electrode pad in the embodiment.

The sensor part 45 receives the electric signal (bioelectric signal) relating to the biological information of the fetus in the mother's body 6. The sensor part 45 is a plate electrode that is formed to substantially have a circular shape in plan view, and as shown in FIGS. 2 to 4, is disposed at the center of the conductive gel sheet 49. As shown in FIG. 5, the second insulating layer 47 is provided around the sensor part 45. With this, the bioelectric signal detected through the conductive gel sheet 49 is incident only on the sensor part 45.

The signal line 46 is connected to the sensor part 45. As shown in FIGS. 2 to 4, the signal line 46 extends to the outside of the outer peripheral edge of the conductive gel sheet 49.

FIG. 3 is a plan view of the first electrode pad 4 when viewed from the release film 50 side. In the following description referring to FIG. 3, the respective directions will be described according to the up, down, right, and left directions on the paper.

As shown in FIG. 3, the signal line 46 extends in a linear shape diagonally upward and right along the radial direction of the conductive gel sheet 49 from a center P1 of the sensor part 45 (conductive gel sheet 49) and extends downward in the end portion thereof when viewed from the release film 50 side. That is, the signal line 46 extends substantially in an L-shape, and is provided with the connection portion 461 at the tip thereof. For this reason, the connection portion 461 is directed downward of FIG. 3. That is, the connection direction of the connector 3 is a surface direction of the adhesive sheet 41, and is a direction different from the extension direction of the signal line 46 from the sensor part 45 to the outer peripheral edge of the conductive gel sheet 49.

Figure 6:
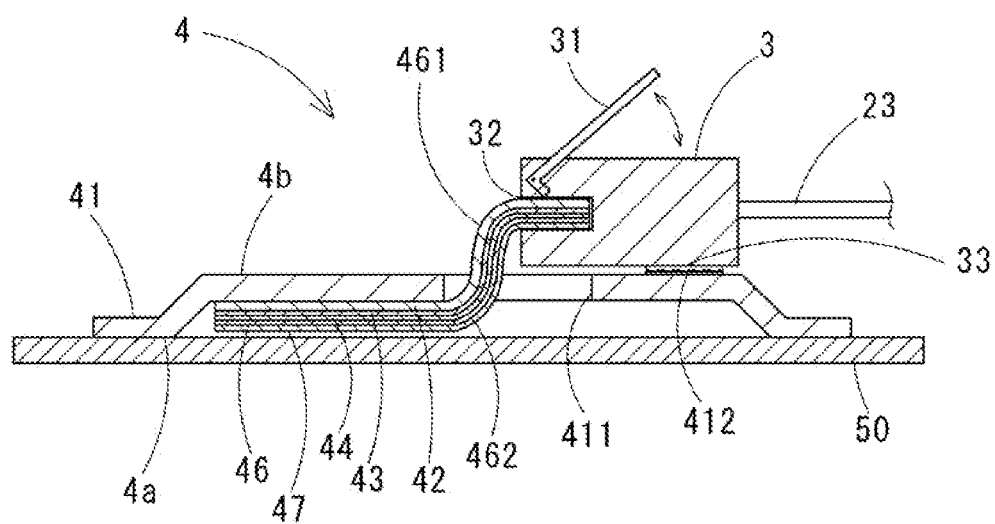
FIG. 6 is a schematic sectional view showing a section of the first electrode pad and the connector taken along a line B1-B1 shown in FIG. 4.

The connection portion 461 is a portion that is connectable to the connector 3, and is formed to substantially have a rectangular shape. As the connection portion 461 is fitted with the connector 3, the bioelectric signal transmitted from the sensor part 45 through the signal line 46 is transmitted to the cable 23. As shown in FIG. 6, the connection portion 461 is connected to the connector 3 on the surface opposite to the adhesive surface through the opening portion 411 of the adhesive sheet 41.

The connection portion 461 is formed by coating the conductive carbon layer 462 (see FIG. 6) with silver or silver chloride. The connection portion 461 can be cut and bent by a slit along with the PET film 42 excluding a portion connected to the signal line 46.

The conductive gel sheet 49 is a conductive sheet that is adherable to the mother's body 6, and is disposed to overlap the sensor part 45 when viewed from the release film 50 side. As described above, the conductive gel sheet 49 is formed to substantially have a circular shape in plan view, and is mounted on the mother's body 6 to transmit the bioelectric signal of the fetus in the mother's body 6 to the sensor part 45.

The release film 50 is disposed to face the outer peripheral edges of the conductive gel sheet 49 and the adhesive sheet 41. As the release film 50 is separated, the conductive gel sheet 49 can be exposed and the first electrode pad 4 can be attached to the mother's body 6. The release film 50 is formed to substantially the same shape as the adhesive sheet 41 in plan view, and is formed to have a size slightly greater than the adhesive sheet 41.

[Configuration of Connector]

The connector 3 is connected to the cable 23, and is provided to be connectable to the connection portion 461 of the first electrode pad 4.

As shown in FIG. 6, the connector 3 includes an opening portion 32 into which the connection portion 461 is inserted, a lock piece 31 to which the connection portion 461 inserted into the opening portion 32 is fixed, and a fixing member 33 that fixes the connector 3 to the first electrode pad 4. The lock piece 31 rotationally moves around an end portion of the lock piece 31 on the opening portion 32 side. In a case where the connection portion 461 is inserted into the opening portion 32 in a state in which the lock piece 31 is erected, and the lock piece 31 is rotationally moved to be pushed down, the connection portion 461 is fixed to the connector 3 and is connected to the cable 23.

As described above, the fixing member 33 is constituted of the hook-raised hook-and-loop fastener, and is attachable to and detachable from the fixing member 412 of the first electrode pad 4. As shown in FIGS. 4 and 6, the fixing member 33 is provided to face the fixing member 412 of the first electrode pad 4 when the connection portion 461 is fixed, and with this, the connector 3, with which the connection portion 461 is fitted, is fixed to the first electrode pad 4.

Although the first electrode pad 4 includes a set of the sensor part 45, the conductive gel sheet 49, and the signal line 46, for example, the first electrode pad 4 may include a plurality of sets. Hereinafter, an electrode pad including a plurality of sensor parts 45 will be described in detail.

[Configuration of Second Electrode Pad]

Figure 7:
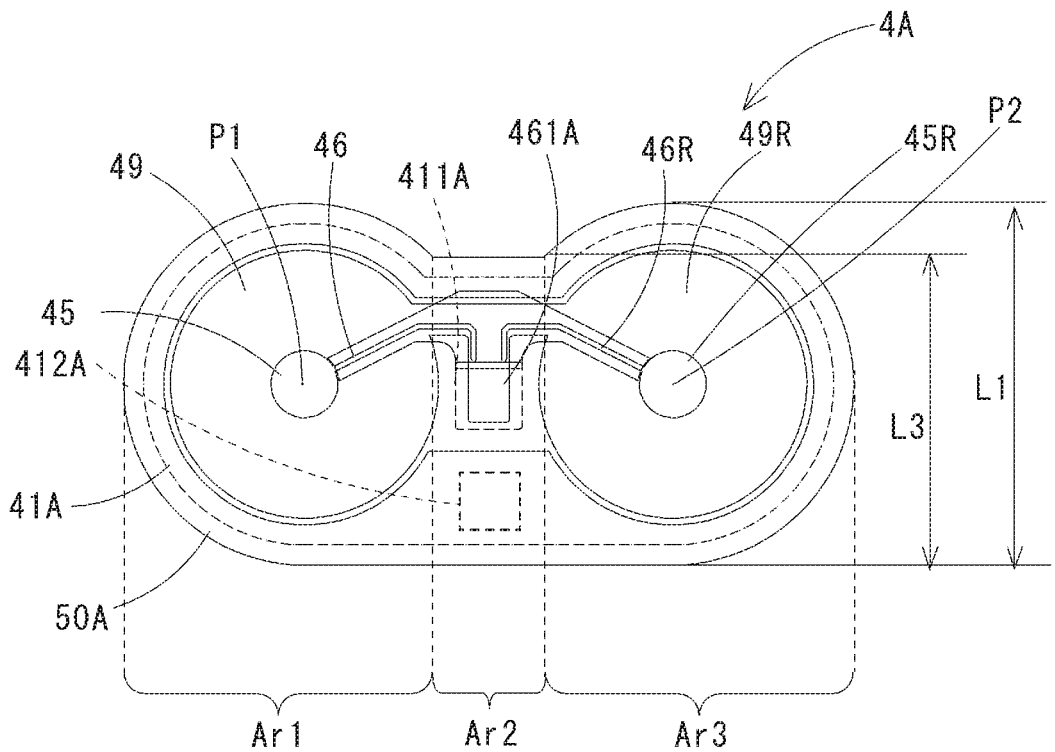
FIG. 7 is a plan view of a second electrode pad that is connected to the biological information detection device in the embodiment when viewed from the release film side.

FIG. 7 is a plan view of a second electrode pad 4A when viewed from a release film 50A side. In the following description, the same or substantially same members as those in the first electrode pad 4 are represented by the same reference numerals, and description will not be repeated. In the description of FIG. 7, the respective directions will be described according to the up, down, right, and left directions on the paper. The same applies to a case of FIG. 8.

As shown in FIG. 7, the second electrode pad 4A has sensor parts 45 and 45R, signal lines 46 and 46R, and conductive gel sheets 49 and 49R. As shown in FIG. 7, an adhesive sheet 41A of the second electrode pad 4A further includes a third area Ar3 where a sensor part 45R, a conductive gel sheet 49R, and a signal line 46R are disposed, in addition to a first area Ar1 including a set of a sensor part 45, a conductive gel sheet 49, and a signal line 46 and a second area Ar2 including a connection portion 461A. The third area Ar3 is disposed on a side opposite to the second area Ar2 from the first area Ar1. For this reason, in the adhesive sheet 41A of the second electrode pad 4A, as shown in FIG. 7, the first area Ar1 and the third area Ar3 are disposed right and left, and the second area Ar2 is disposed between the first area Ar1 and the third area Ar3. Among these, the first area Ar1 and the second area Ar2 have the same configuration as in the first electrode pad 4, the third area Ar3 has the same configuration as a layer structure of the first electrode pad 4 shown in FIG. 5 and has a shape along the outer peripheral edge of the conductive gel sheet 49R. The third area Ar3 is formed to be greater than the outer peripheral edge of the conductive gel sheet 49R and is formed to substantially have a circular shape in plan view.

As described above, the signal line 46 of the first area Ar1 extends in a linear shape diagonally upward and right along the radial direction of the conductive gel sheet 49 from the center P1 of the sensor part 45 in the first area Ar1 and extends downward in the end portion thereof when viewed from the release film 50A side.

As shown in FIG. 7, the signal line 46R of the third area Ar3 extends in a linear shape diagonally upward and left along the radial direction of the conductive gel sheet 49R from a center P2 of the sensor part 45R in the third area Ar3 and extends downward in the end portion thereof when viewed from the release film 50A side. That is, the signal lines 46 and 46R extends substantially in an L-shape, and the tip portions thereof are bundled. The connection portion 461A is provided at a tip of a portion where the signal lines 46 and 46R are bundled. For this reason, an extension direction of the connection portion 461A is directed downward of FIG. 7. That is, the connection direction of the connector 3 is a surface direction of the adhesive sheet 41A and is a direction different from the extension direction of the signal lines 46 and 46R from the sensor parts 45 and 45R to the outer peripheral edges of the conductive gel sheets 49 and 49R.

The connection portion 461A is positioned between the adjacent conductive gel sheets 49 and 49R in the adhesive sheet 41A. One connection portion 461A is provided for a plurality of signal lines 46 and 46R.

With such a configuration, in plan view of the adhesive sheet 41A, a maximum dimension L3 of the area (second area Ar2) in the adhesive sheet 41A, in which the connector 3 is provided, in the up-down direction (the direction along the connection direction of the connector 3 to the connection portion 461) is smaller than a maximum dimension L1 of the area (the first or third area Ar1 or Ar3), in which the conductive gel sheet 49 or 49R are provided, in the up-down direction.

In the second area Ar2, an opening portion 411A and a fixing member 412A having the same shapes as the opening portion 411 and the fixing member 412, respectively, are provided. That is, the connection portion 461A, the opening portion 411A, and the fixing member 412A are provided in a portion that becomes a blank space between the two conductive gel sheets 49.

In a case where the connection portion 461A is connected to the connector 3, the bioelectric signals detected by the sensor parts 45 and 45R through the conductive gel sheets 49 and 49R are transmitted to the connector 3 through the signal lines 46 and 46R and the connection portion 461A.

[Configuration of Third Electrode Pad]

Figure 8:
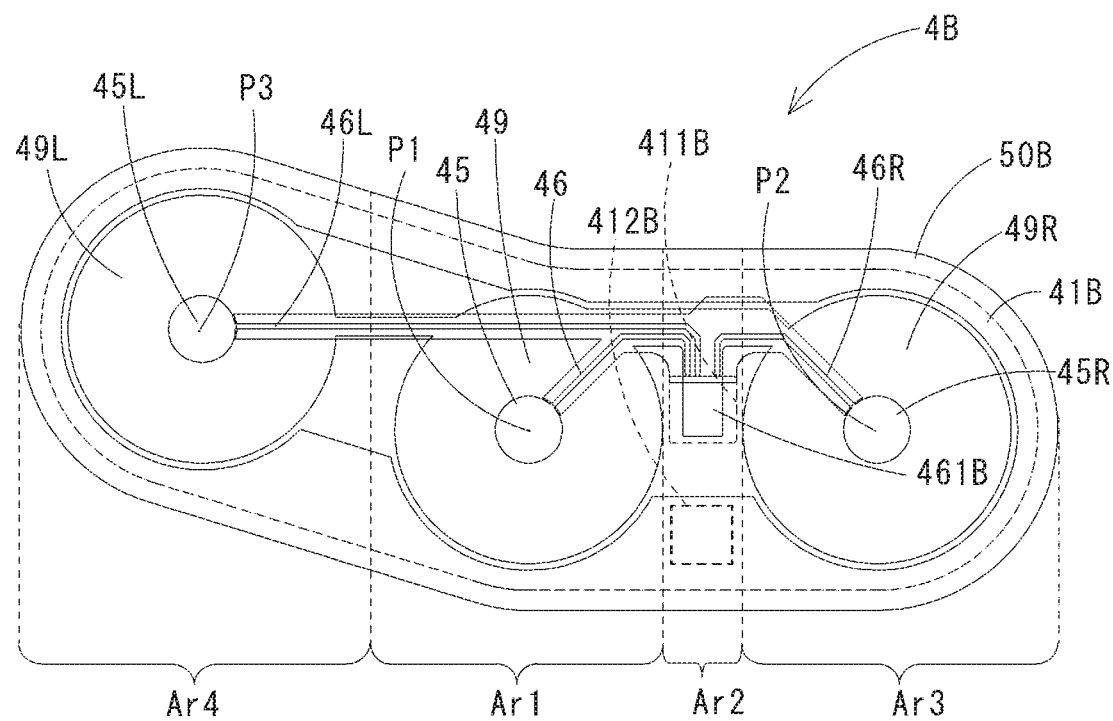
FIG. 8 is a plan view of a third electrode pad that is connected to the biological information detection device in the embodiment when viewed from the release film side.

FIG. 8 is a plan view of a third electrode pad 4B when viewed from a release film 50B side.

As shown in FIG. 8, the third electrode pad 4B has sensor parts 45, 45R, and 45L, signal lines 46, 46R, and 46L, and conductive gel sheets 49, 49R, and 49L. An adhesive sheet 41B of the third electrode pad 4B is formed to substantially have a V-shape in plan view, and as shown in FIG. 8, further includes a fourth area Ar4 including a set of the sensor part 45L, the conductive gel sheet 49L, and the signal line 46L, in addition to a first area Ar1 including a set of the sensor part 45, the conductive gel sheet 49, and the signal line 46, a second area Ar2 including a connection portion 461B, and a third area Ar3 including a set of the sensor part 45R, the conductive gel sheet 49R, and the signal line 46R.

The fourth area Ar4 is disposed on a diagonally upper left side of the first area Ar1. For this reason, in the adhesive sheet 41B of the third electrode pad 4B, the fourth area Ar4 and the third area Ar3 are disposed at both right and left ends, and the first area Ar1 and the second area Ar2 are disposed between the fourth area Ar4 and the third area Ar3. Among these, the first to third areas Ar1, Ar2, and Ar3 have the same configuration as in the second electrode pad 4A. The fourth area Ar4 has the same configuration as the layer structure of the first electrode pad 4 shown in FIG. 5 and has a shape along the outer peripheral edge of the conductive gel sheet 49L. The fourth area Ar4 is formed to be greater than the outer peripheral edge of the conductive gel sheet 49L and is formed to substantially have a circular shape in plan view. Since the fourth area Ar4 is disposed on an upper side than the first to third areas Ar1 to Ar3, a center P3 of the sensor part 45L is positioned on an upper side than the centers P1 and P2 of the sensor parts 45 and 45R.

As described above, the signal line 46 of the first area Ar1 extends in a linear shape diagonally upward and right along the radial direction of the conductive gel sheet 49 from the center P1 of the sensor part 45 in the first area Ar1 when viewed from the release film 50B side. The signal line 46R of the third area Ar3 extends in a linear shape diagonally upward and left along the radial direction of the conductive gel sheet 49R from the center P2 of the sensor part 45R in the third area Ar3 when viewed from the release film 50B side.

As shown in FIG. 8, the signal line 46L of the fourth area Ar4 extends in a linear shape right from the center P3 of the sensor part 45L, crosses a part of the conductive gel sheet 49, and extends to the same position as the tips of the signal lines 46 and 46R when viewed from the release film 50B side. The signal lines 46, 46R, and 46L extend substantially in an L-shape, and the tip portions thereof are bundled. The connection portion 461B is provided at a tip of a portion where the signal lines 46, 46R, and 46L are bundled. For this reason, the extension direction of the connection portion 461B is directed downward of FIG. 8. That is, the connection directions of the connectors 3 are a surface direction of the adhesive sheet 41B and are directions different from the extension directions of the signal lines 46, 46R, and 46L from the sensor parts 45, 45R, and 45L to the outer peripheral edges of the conductive gel sheets 49, 49R, and 49L.

The connection portion 461B is positioned between the adjacent conductive gel sheets 49 and 49R in the adhesive sheet 41B. One connection portion 461B is provided for a plurality of signal lines 46, 46R, and 46L.

In the third electrode pad 4B, in plan view of the adhesive sheet 41B, a maximum dimension of the area in the adhesive sheet 41B, in which the connector 3 is provided, in the up-down direction (the direction along the connection direction of the connector 3 to the connection portion 461B) is the same as a maximum dimension of each of the areas Ar1 and Ar3, in which the conductive gel sheets 49 and 49R are provided, respectively, in the up-down direction, and a maximum dimension of the fourth area Ar4, in which the conductive gel sheet 49L is provided, in the up-down direction is greater than the above-described maximum dimension.

In the second area Ar2, an opening portion 411B and a fixing member 412B having the same shapes as the opening portion 411 and the fixing member 412, respectively, are provided. That is, the connection portion 461B, the opening portion 411B, and the fixing member 412B are provided in a portion that becomes a blank space between the two adjacent conductive gel sheets 49.

In a case where the connection portion 461B is connected to the connector 3, the bioelectric signals detected by the sensor parts 45, 45R, and 45L through the conductive gel sheets 49, 49R, and 49L are transmitted to the connector 3 through the signal lines 46, 46R, and 46L and the connection portion 461B.

[Method of Mounting Electrode Pad]

Figure 9:
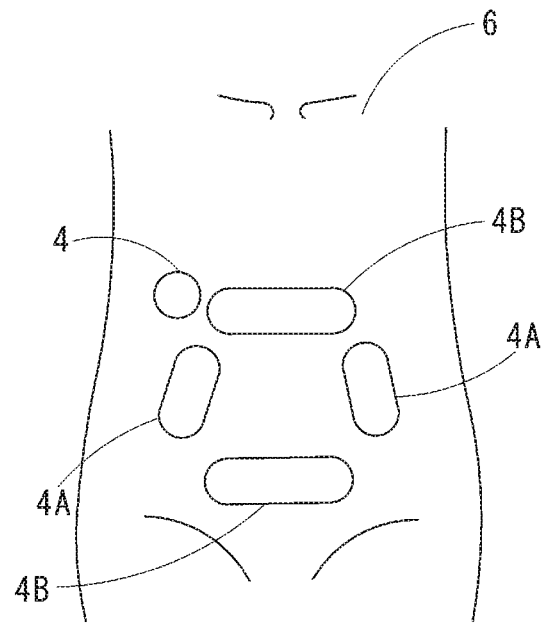
FIG. 9 is a diagram showing an example where each electrode pad in the embodiment is mounted on a mother's body.

As shown in FIG. 9, the electrode pads 4, 4A, and 4B are mounted on the mother's body 6. For example, as shown in FIG. 9, one first electrode pad 4, two second electrode pads 4A, and two third electrode pads 4B are mounted on an abdominal region of the mother's body 6. Then, the corresponding connectors 3 are connected to the connection portions 461, 461A, and 461B of the electrode pads 4, 4A, and 4B. In this case, the fixing members 33 of the connectors 3 are pressed and fixed to the fixing members 412, 412A, and 412B of the electrode pads 4, 4A, and 4B, respectively. Then, detection of the bioelectric signal of the fetus is executed.

In the above-described embodiment, the electrode pads 4, 4A, and 4B that are able to be mounted on the mother's body 6 and the connectors 3 that are connectable to the electrode pads 4, 4A, and 4B are provided with the fixing members 412, 412A, and 412B that are attachable to and detachable from each other. Thus, it is possible to fix the connectors 3 fitted with the electrode pads 4, 4A, and 4B to the electrode pads 4, 4A, and 4B, and even though there is the movement of the mother's body 6 or the movement of the fetus in the mother's body 6 in detecting the bioelectric signals of the fetus in the mother's body 6 with the electrode pads 4, 4A, and 4B and even though the cable 23 is pulled, it is possible to restrain noise from being mixed with the detected bioelectric signals.

Since the position of the sensor part 45, 45R, or 45L and the connection position of the connector 3 are offset, it is possible to restrain the pressure at the time of the connection of the connector 3 or shake of the cable from acting directly on the sensor part 45, 45R, or 45L. With this, it is possible to suppress shake or movement of the sensor part 45, 45R, or 45L, and to restrain noise from being mixed with the bioelectric signal.

Since the fixing member 412, 412A, or 412B can be disposed on the surface of the adhesive sheet 41, 41A, or 41B constituting the electrode pad 4, 4A, or 4B opposite to the adhesive surface, it is possible to facilitate attachment and detachment of the connector 3 to and from the electrode pad 4, 4A, or 4B.

Since the second electrode pad 4A or the third electrode pad 4B include a plurality of sensor parts 45, 45R, or 45L, it is possible to detect more bioelectric signals of the fetus in the mother's body 6 with a plurality of sensor parts 45, 45R, and 45L.

Since the second electrode pad 4A or the third electrode pad 4B is provided with only one connection portion 461A or 461B, and the connection portion 461A or 461B is positioned between the adjacent conductive gel sheets 49 and 49R, it is possible to reduce the size of the electrode pad 4A or 4B compared to a case where the connection portion is provided for each of the signal lines 46, 46R, and 46L. Since the number of connection portions 461A or 461B is one, it is possible to reduce the number of connectors 3 and the number of cables 23, and to restrain noise from being mixed with the detected bioelectric signals.

The connection direction of the connector 3 is the direction different from the extension direction of the signal line 46, 46L, or 46R from the sensor part 45, 45R, or 45L to the outer peripheral edge of the conductive gel sheet 49, 49R, or 49L. Thus, in a case where the fixing members 412, 412A, and 412B are disposed at positions adjacent to the opening portions 411, 411A, and 411B, the shape of the adhesive sheet 41, 41A, or 41B is not elongated in the extension direction of the signal line 46, 46R, or 46L from the sensor part 45, 45R, or 45L to the outer peripheral edge of the conductive gel sheet 49, 49R, or 49L, and the maximum dimension L2 or L3 in the adhesive sheet 41, 41A, or 41B along the connection direction of the connector 3 can be equal to or smaller than the maximum dimension L1 of the areas, in which the conductive gel sheet 49, 49R, or 49L, in the above-described direction. That is, it is possible to reduce the size of the electrode pad 4, 4A, or 4B.

Even though the connector 3 is connected to the connection portion 461, 461A, or 461B, since force generated due to the connection of the connector 3 is not applied directly to the signal line 46, 46R, or 46L and the sensor part 45, 45R, or 45L, it is possible to reduce a possibility that the electrode pad 4, 4A, or 4B is demounted from the mother's body 6, and the electrode pad 4, 4A, or 4B is damaged.

As the electromagnetic shield layer 43 is provided between the adhesive surface and the sensor part 45, the sensor part 45 is hardly affected by electromagnetic waves, it is possible to further restrain noise from being mixed with the signal relating to the biological information detected by the sensor part 45.

Since the fixing member 33, 412, 412A, or 412B is constituted of the hook-and-loop fastener, it is possible to facilitate attachment and detachment of the electrode pad 4, 4A, or 4B and the connector 3.

Figure 10:
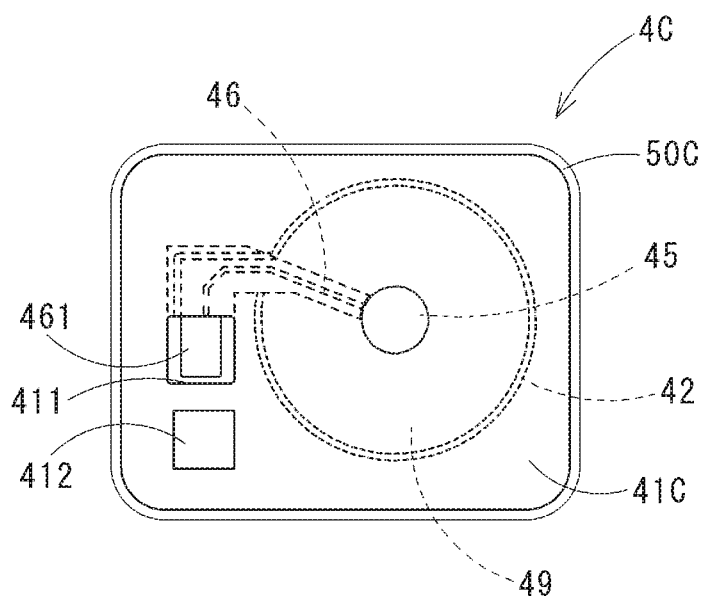
FIG. 10 is a plan view showing a modification example of an electrode pad in the embodiment.

The present invention is not limited to the above-described embodiment, and various alterations can be added without departing from the spirit and scope of the present invention. For example, in the above-described embodiment, although the first electrode pad 4 is configured such that the maximum dimension L2 of the area (second area Ar2) in the adhesive sheet 41, in which the connector 3 is provided, along the connection direction of the connector 3 is smaller than the maximum dimension L1 of the area (first area Ar1), in which the conductive gel sheet 49 is provided, along the connection direction of the connector 3, the present invention is not limited thereto, and for example, the first electrode pad 4 may have a shape shown in FIG. 10.

A first electrode pad 4C according to the modification example is configured such that each of an adhesive sheet 41C and a release film 50C is formed to substantially have a rectangular shape. In this case, a maximum dimension of an area in the adhesive sheet 41C, in which the connector 3 is provided, along the connection direction of the connector 3 becomes equal to a maximum dimension of an area, in which the conductive gel sheet 49 is provided, along the connection direction of the connector 3. Even in this case, it is possible to obtain the same effects as in the above-described embodiment.

In the above-described embodiment, although the electrode pad including a maximum of the three sensor parts 45, 45R, and 45L is illustrated, the present invention is not limited thereto, and for example, an electrode pad may include four or more sensor parts. In this case, a plurality of connection portions 461, such as one connection portion 461 for every two sensor parts 45, may be provided.

In the above-described embodiment, although the fixing member 33 is the densely loop-raised hook-and-loop fastener, and the fixing member 412 is the hook-raised hook-and-loop fastener, the present invention is not limited, and the densely loop-raised hook-and-loop fastener and the hook-raised hook-and-loop fastener may be reversed or both hooks and loops may be implanted and a shape with no distinction between hook surfaces and loop surfaces may be made.

In the above-described embodiment, although the subject is the fetus in the mother's body 6, the present invention is not limited thereto, and the subject may be an infant, an adult, or the like other than the mother's body.

INDUSTRIAL APPLICABILITY

It is possible to restrain noise from being mixed with a signal relating to biological information.

What is claimed is:

1. A biological information detection device comprising:
an electrode pad configured to detect a signal relating to biological information of a subject;
a connector that is connectable to the electrode pad to receive the signal from the electrode pad;
a cable that is connected to the connector for transmission of the signal from the connector; and
first and second fixing members provided, respectively, with the electrode pad and the connector and configured such that the first and second fixing member are attachable to and detachable from each other to detachably secure the electrode pad and the connector together, wherein
the electrode pad includes an adhesive sheet having an adhesive surface on one surface of the adhesive sheet and a non-adhesive surface on the other surface thereof, a sensor configured to detect the signal and positioned on the adhesive surface, an adherable conductive gel sheet disposed to have the sensor between the conductive gel sheet and the adhesive surface of the adhesive sheet, a signal line connected to the sensor and extensive from the sensor through an outside of an outer peripheral edge of the conductive gel sheet, and a connection portion provided at a tip of the signal line and connectable to the connector,
the adhesive sheet has an opening portion through which the connection portion comes out from a side of the adhesive surface of the adhesive sheet to a side of the non-adhesive surface thereof,
the first fixing member is disposed adjacent to the opening portion on the non-adhesive surface of the adhesive sheet,
the connector and the connection portion of the signal line are arranged to mate in a connection direction that is extensive along the adhesive sheet but is different from a signal line extension direction in which the signal line extends from the sensor to the outer peripheral edge of the conductive gel sheet, wherein a lesser one of angles formed at an intersection between the connection direction and the signal line extension direction is less than 90 degrees in a plan view, and
in the plan view, the adhesive sheet comprises a first area (Ar1) and a second area (Ar2), the first area (Ar1) being at least as large as the conductive gel sheet to cover the conductive gel sheet, the second area (Ar2) being located adjacent to the first area (Ar1) on which the connection portion and the first fixing member are placed, wherein a maximum dimension (L2) of the second area (Ar2) measured in the connection direction is equal to or smaller than a maximum dimension (L1) of the first area (Ar1) measured in the connection direction.

2. The biological information detection device according to claim 1,
wherein the electrode pad has a plurality of the sensors, a plurality of the conductive gel sheets, and a plurality of the signal lines,
the plurality of the signal lines are bundled,
the connection portion is provided at a tip of each signal line at a location where the signal lines are bundled, and
the connection portion is positioned between two adjacent conductive gel sheets in the adhesive sheet.

3. The biological information detection device according to claim 1, wherein the electrode pad has an electromagnetic shield layer between the adhesive surface and the sensor so as to covers the sensor.

4. The biological information detection device according to claim 1, wherein the first and second fixing members are each constituted of a hook-and-loop fastener.

* * * * *